United States Patent
Ansara et al.

(10) Patent No.: US 6,939,552 B2
(45) Date of Patent: Sep. 6, 2005

(54) DUAL COMPARTMENT PACKAGED COSMETIC COMPOSITION

(75) Inventors: Carol Ansara, Durban (ZA); Ursula Cooper, Kwazulu-Natal (ZA)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 313 days.

(21) Appl. No.: 10/214,632

(22) Filed: Aug. 8, 2002

(65) Prior Publication Data

US 2003/0068287 A1 Apr. 10, 2003

(30) Foreign Application Priority Data

Aug. 14, 2001 (GB) .............................. 0119831

(51) Int. Cl.[7] .................................. A61K 7/00
(52) U.S. Cl. ......................... 424/401; 424/59; 424/62; 514/844; 514/845; 514/846
(58) Field of Search ............................ 424/651, 59, 62; 514/844, 846, 845

(56) References Cited

U.S. PATENT DOCUMENTS

| | | | |
|---|---|---|---|
| 3,080,293 A | 3/1963 | Koff | |
| 4,096,240 A | 6/1978 | Mathur | |
| 5,914,116 A | 6/1999 | Suares et al. | |
| 6,153,177 A | 11/2000 | Bartolone et al. | |

FOREIGN PATENT DOCUMENTS

| | | |
|---|---|---|
| EP | 0 396 422 | 5/1990 |
| GB | 2 230 186 | 10/1990 |
| WO | 00/35414 | 6/2000 |

OTHER PUBLICATIONS

International Search Report PCT/EP/09110, Dec. 8, 2002.

*Primary Examiner*—Thurman K. Page
*Assistant Examiner*—Lakshmi Channavajjala
(74) *Attorney, Agent, or Firm*—Milton L. Honig

(57) ABSTRACT

A cosmetic skin lightening product delivered from a dual-chamber package is provided wherein separate first and second compositions are filled into the respective compartments. Both compositions contain stearic acid and a skin lightening agent, except that the first composition contains a higher amount of stearic acid than the second composition. Preferably, the second composition will have a higher viscosity than that of the first. A more effective skin lightening is achieved by the sequential application to an effected area of these physically different compositions.

5 Claims, No Drawings

DUAL COMPARTMENT PACKAGED COSMETIC COMPOSITION

The invention concerns cosmetic compositions for lightening skin color.

A variety of products exist for helping consumers arrive at a whiter skin complexion. The literature describes these products and related approaches. For instance, U.S. Pat. No. 4,096,240 (Mathur) reports the combination of niacinamide and sunscreens, EP 0 396 422 (Natraj et al.) describes enhancement of niacinamide performance through formulations containing a silicone compound and both a UVA and UVB sunscreen.

Treatment regimes are reported in U.S. Pat. No. 5,914,116 (Suares et al.). The patent discloses dual compartment packages for sequential delivery of first and second active materials. Among listed actives are skin lighteners such as niacinamide. This disclosure places emphasis on the actives but provides very little instruction on selection of the best carrier systems. Indeed, no consideration is given to the possible beneficial impact potentially available through selection of carriers for the actives.

Some consumers, especially those with dark complexion have a very oily skin. Whitening products must be formulated to also address the oiliness complication.

Accordingly, it is an advantage of the present invention to provide a skin lightening product with improved effectiveness.

Another advantage of the present invention is to provide a skin lightening product operative on oily skin and providing sufficient moisturization during evening hours.

These and other advantages of the present invention will become more readily apparent through consideration of the following summary and detailed discussion.

According to a first aspect of the invention, there is provided a cosmetic skin lightening product delivered from a dual chamber package which includes:

(A) a first composition within a first chamber of the dual chamber package, the composition including:
(i) from about 5 to about 50% of stearic acid by weight of the first composition;
(ii) from about 0.01 to about 110% of a skin lightening agent by weight of the first composition;
(B) a second composition within a second chamber of the dual-chamber package, the second composition including
(i) from about 0.01 to about 40% of stearic acid by weight of the second composition;
(ii) from about 0.01 to about 10% of a skin lightening agent by weight of the second composition; and
wherein the stearic acid is present in a higher amount in the first than in the second composition.

Not only actives but vehicles delivering those actives in sequential application from separate dual-chamber packaged compositions can have a significant impact upon performance. More specifically, advantages of the present invention are achieved by applying a first skin lightening composition characterized by a high stearic acid base carrier to an intended treatment area. A second composition containing a further amount of skin lightening agent in a relatively low stearic acid content base carrier is subsequently applied to the treatment area. The first and second treatments preferably are applied respectively during daylight and nighttime hours. Sequential application of these compositions results in an optimum fairness improvement over application of the separate compositions. More specifically, the high stearic acid base carrier imparts the skin with a good appearance (improved skin fairness). In a complementary fashion, the low stearic acid content base carrier facilitates transference of the skin lightening actives into the epidermis. Thus, the system of this invention provides an optimum combination of appearance and delivery benefits.

The first composition of the present invention will have levels of stearic acid ranging from about 5% to about 50%, preferably from about 10 to about 40%, optimally from about to about 25% by weight of the first composition. The second composition will have levels of stearic acid ranging from about 0.01 to about 40%, preferably from about 0.5 to about 20%, optimally from about 1 to about 4% by weight of the second composition.

Advantageously the stearic acid may be present as asymmetric solid particles. Asymmetric is understood to mean that at least two of three dimensions on a majority of the particles are not size identical. These particles can be oval or plate-like. Average particle size along greatest length may range from about 0.01 to about 500 micron and preferably from about 1 to about 100 micron. The particles are employed in the composition to impart a cream-like viscosity. By virtue of being asymmetric, the particles deliver high skin friction. The term "acid" as employed herein does not exclude the presence of a salt of stearic acid depending upon the pH of the final composition. For instance, sodium, potassium or ammonium salts may be present. The salt amount is included in the amount of fatty acid. Most preferably, however, the stearic acid is present in its non-salt form.

First and second compositions of the present invention may have a viscosity which can range from about 40 Pascal-second (PaS) at a shear rate of 1 reciprocal second (1/s), preferably in a viscosity ranging from about 40 PaS to about 300 PaS, more preferably from about 60 to about 120 PaS. Viscosity is measured using any viscometer or Rheometer with a shear rate of 1/s, at ambient temperature 25° C. Suitable viscometers/rheometers are Brookfield, Haake and is Bohlin with cone and plate fixtures. Viscosity of the second composition preferably is higher than that of the first to ensure higher moisturization.

First and second compositions are separately but sequentially applied to a skin treatment area. Usually the first composition is permitted to remain on the treatment area for 1 to 48 hours, but preferably 6 to 12 hours before application of the second composition. Advantageously, the sequential use can be in the form of a day and night time application, respectively. Consumers may be alerted to this sequential treatment regime by instructions provided with the packaging of the compositions.

Another useful component of compositions according to the present invention is that of an emollient, especially a liquid oil emollient. Amounts of the emollient may range from about 0.1 to about 40%, preferably from about 1 to about 30%, optimally from about 5 to about 25% by weight of each of the first and second compositions. In particular, the amount of emollient present in the second composition advantageously is in a higher amount than in the first composition.

Emollients may be selected from hydrocarbons, esters, $C_8$–$C_{60}$ alcohols, ethers, silicones and combinations thereof. Hydrocarbons suitable for the invention include petrolatum, mineral oil, isoparaffins, polyalpha-olefins and polybutenes. Liquid oil emollients are preferred. By term "liquid" is meant a material pourable at 25° C.

Suitable esters include both natural and synthetic materials. Among the natural esters are triglyceride oils such as castor oil, safflower oil, cottonseed oil, corn oil, olive oil, cod liver oil, almond oil, avocado oil, palm oil, sesame oil, squalene and maleated soybean oil. Mono- and di- glycerides may also be employed. Illustrative are glycerol monostearate, glycerol di-stearate, glycerol monopalmitate, glycerol monolaurate, glycerol di-laurate, glycerol di-palmitate, glycerol mono-oleate and combinations thereof.

Synthetic esters are represented by $C_1$–$C_{24}$ alkyl and alkenyl esters of $C_{10}$–$C_{24}$ fatty acids.

Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, dilsohexyl adipate, dihexyldecyl adipate, diisopropyl sebacate, lauryl lactate, myristyl lactate, cetyl lactate, oleyl myristate, oleyl stearate, oleyl oleate, isopropyl myristate, isostearyl palmitate, tridecyl salicylate, $C_{12}$–$C_{15}$ alkyl benzoate and combinations thereof.

Suitable fatty alcohols may be those with from 10 to 24 carbon atoms. Illustrative are lauryl, myristyl, cetyl, hexadecyl, stearyl, isostearyl, hydroxystearyl, oleyl, ricinoleyl, behenyl, erucyl, 2-octyl dodecanyl alcohols and mixtures thereof.

Emollients may also include fatty alcohol ethers. These may include ethoxylated or non-ethoxylated fatty alcohols of 10 to 24 carbon atoms including the lauryl, cetyl, stearyl, isostearyl, oleyl and cholesterol alcohols. When ethoxylated the alcohols have attached thereto from 1 to 50 ethylene oxide groups and/or 1 to 50 propylene oxide groups. Most preferred is dicapryl ether commercially available as Cetiol® OE.

Silicone oils may be useful emollients. These can include dimethyl polysiloxane, methyl phenyl polysiloxane and alkoxylated siloxanes (dimethicone copolyols). Particularly preferred are cyclomethicone, dimethicone and combinations thereof.

An important component of each of the first and second compositions is that of a skin lightening agent. Illustrative agents Include niacinamide, kojic acid, hydroquinone, ferulic acid and esters, placental extract, lactic acid, arbutin and combinations thereof. Amounts of the skin lightening agent may range from about 0.01 to about 10%, preferably from about 01 to about 7%, optimally from about 1 to about 4% is by weight of each of the first and second compositions.

Sunscreen agents may be incorporated into one or both of the compositions. The term "sunscreen" is used to denote ultraviolet ray-blocking compounds inhibiting absorption within the wavelength region between 290 and 420 nm. These compounds may either be organic or inorganic. The organic compounds are preferred. When the sunscreen is inorganic and serves as the sole sun protective substance, it should be present at levels ranging from about 5 to 30%, preferably from about 8 to 15% by weight.

Typical inorganic sunscreens include titanium dioxide, zinc oxide, iron oxide and combinations thereof. Most preferred is titanium dioxide, especially having an average particle size no higher than 700 nm, preferably no higher than 200 nm, optimally less than 35 nm.

Organic sunscreens may be classified into five groups based upon their chemical structures; para-amino benzoates; salicylates; cinnamates; benzophenones; coumarins; azoles and miscellaneous chemicals including menthyl anthralinate. Also polymeric particles may be useful such as polyethylene and polyamides. Organic sunscreen compound will range in amount anywhere from about 0.1 to about 25%, optimally from about 1 to about 15%, more preferably from about 5 to about 10% by weight. Preferred sunscreen compounds are octyl methoxy cinnamate and Avobenzone, commercially available respectively as Parsol MCX® and Parsol 1789®.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, ethoxylated glycerol, propoxylated glycerol and mixtures thereof, For best results the humectant is preferably glycerol. The amount of humectant may range anywhere from about 0.1 to about 40%, preferably between about 1 and about 15% by weight of the first or second composition.

Both first and second compositions of the invention can also include thickeners/viscosifiers in amounts from about 0.01 to about 10% by weight of the composition. As known to those skilled in the art, the precise amount of thickeners can vary depending upon the consistency and thickness of the composition which is desired. Exemplary thickeners are magnesium aluminum silicate (Veegum®), guar gums (such as Jaguar HP-120®), xanthan gum, sodium carboxymethyl cellulose, hydroxyalkyl and alkyl celluloses, and crosslinked acrylic acid polymers such as those sold by B. F. Goodrich under the Carbopol® trademark, Preservatives can desirably be incorporated into both the first and second compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, imidazolidinyl urea, sodium dehydroxyacetate, propyl paraben and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

When present, the amount of water in the first and second compositions may range anywhere from about 1 to about 99%, preferably from about 20 to about 90%, optimally between about 40 and 70% by weight, Emulsifiers can be included in both first and second compositions. These materials may be selected from nonionic, anionic, cationic or amphoteric emulsifying agents. Amounts of these materials may range from about 0.1 to about 30%, preferably from about 1 to about 15% by weight of each of the compositions. Illustrative of the nonionic surfactants are alkoxylated compounds based upon $C_8$–$C_{22}$ fatty alcohols, $C_8$–$C_{22}$ fatty acids and sorbitan. Particularly preferred are Ceteth-20 and Ceteareth-6.

A variety of skin benefit agents may also be included within the compositions. Illustrative are retinoids, ceramides, phytosphingosines, alpha-hydroxy acids, and combinations thereof. Most preferred are retinoids such as retinol and the $C_1-C_{20}$ esters of retinol. Amounts of any of these materials may range from 0.00001 to 10%, preferably from 0.01 to 1% by weight of the respective compositions.

A wide variety of proteins may also supplement the compositions. For instance, hydrolyzed milk protein (p-Casitose available from Warkem) may be useful. Amounts of protein may range from about 0.001 to about 1%, preferably from about 0.05 to about 0.5% by weight of one or both of the compositions.

Products according to the present invention will be delivered through a dual-compartment package wherein first and second compositions are stored separately from one another prior to being dispensed. Most preferred is a vertically stacked double-jar arrangement with the upper jar screw threadedly joined to the lower one as illustrated in U.S. Pat. No. 5,914,116 herein incorporated by reference. An alternate pumpable package embodiment wherein two separate compartmented pumps are joined together with their nozzles pointing in a 180° direction opposite one another is found in U.S. Pat. No. 5,914,116 and in U.S. Pat. No. 5,740,947 (Flaig et al.), both of which are herein incorporated by reference.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The following examples will more fully illustrate the embodiments of this invention. All parts, percentages and proportions referred to herein and in the appended claims are by weight unless otherwise illustrated.

EXAMPLE 1

A preferred embodiment of the present invention utilizes first and second compositions described in Table I and II, respectively.

TABLE I

First Composition

| CHEMICAL NAME | TRADE NAME | WEIGHT % |
|---|---|---|
| Methyl p-hydroxybenzoate | Methyl Paraben | 0.20 |
| Disodium EDTA | Dissolvine NA-2 | 0.04 |
| Glycerol (Vegetable) | Pricerne 9091 | 1.00 |
| Potassium Hydroxide | Potassium Hydroxide | 0.48 |
| Stearic Acid | Pristerene 4911 | 17.90 |
| Propyl-p-hydroxybenzoate | Propyl Paraben | 0.10 |
| Cetyl Alcohol | Cetyl Alcohol | 0.53 |
| Dimethicone | Silicone DC 200/200 | 0.50 |
| Isopropyl Myristate | Crodamol IPM | 0.75 |
| Butylmethoxydibenzoyl Methane | Parsol 1789 | 0.40 |
| Octylmethoxycinnamate | Parsol MCX | 0.75 |
| DL-alpha-Tocopheryl Acetate | Vitamin E Acetate | 0.01 |
| Titanium Dioxide in 40% IPM Dispersion | Tiovell IPM | 0.50 |
| Nicotinamide | Niacinamide | 1.00 |
| Hydrolyzed Milk Protein | p-Casitose | 0.10 |
| 2-Phenyoxyethanol | Phenoxetol | 0.40 |
| Water | Water | balance |

TABLE II

Second Composition

| CHEMICAL NAME | TRADE NAME | WEIGHT % |
|---|---|---|
| Methyl p-hydroxybenzoate | Methyl Paraben | 0.15 |
| Disodium EDTA | Dissolvine NA-2 | 0.05 |
| Glycerine (Vegetable) | Pricerne 9091 | 3.00 |
| Triethanolamine | TEA | 0.55 |
| Stearic Acid | Pristerene 4911 | 3.00 |
| Propyl p-Hydroxybenzoate | Propyl Paraben | 0.10 |
| Carbomer 934 | Carbopol 934 | 0.30 |
| Silicone Oil | Silicone DC 200 | 0.50 |
| Isopropyl Myristate | Crodamol IPM | 0.25 |
| Butylmethoxydibenzoyl Methane | Parsol 1789 | 0.40 |
| Octylmethoxycinnamate | Parsol MCX | 1.25 |
| DL-Alpha-Tocopheryl Acetate | Vitamin E Acetate | 0.10 |
| Titanium Dioxide in 40% IPM Dispersion | Tioveil IPM | 0.50 |
| Nicotinamide | Niacinamide | 1.00 |
| Hydrolyzed Milk Protein | p-Casitose | 0.10 |
| 2-Phenoxyethanol | Phenoxetol | 0.40 |
| Ceteareth-6 & Stearyl Alcohol | Cremophor A6 | 2.50 |
| Ceteth 20 | Brij 58 | 0.60 |
| Petrolatum | White PJ | 5.00 |
| Mineral Oil | WOM 14 | 7.50 |
| Glycerol Monostearate | GMS 40 | 3.00 |
| Butyl Hydroxy Toluene | BHT | 0.05 |
| Water | Water | Balance |

First and second compositions are packaged in respective upper and lower compartments of a dual-compartment stackable jar set. In use the first composition is applied to an area of the face requiring treatment to improve skin fairness. Application is performed during daylight hours. Thereafter, the second composition is applied to the same area of the skin, particularly over periods in night hours. Between application of first and second compositions, the treated area may be cleansed with a cleansing composition.

EXAMPLE 2

Variable Illumination Angle Photography

A clinical evaluation was performed to determine the effectiveness in promoting skin fairness (whitening) using the first and second compositions (Samples A and B, respectively) outlined under Tables I and II of the first Example. Variable Illumination Angle Photography was employed to measure performance differences.

An image collection approach was utilized which exploited the concept that, apart from coherence effects, images collected with linear detectors under different lighting conditions can be added to produce the same image that would be observed if all lights were on simultaneously. In this manner, several images were collected with directional illumination. These images were then added together to create an image with diffuse illumination. The crow's foot region adjacent the eyes was focused upon as treatment area.

Eight fiber ends were mounted in a semi-circle so that they all illuminated the same spot. A shutter was mounted in front of each fiber bundle tip. The semi-circle illuminator was tilted approximately 20 degrees above horizontal and a video camera aimed under it with a fixed focus on the illumination area. The shutters and the camera were under computer control. In approximately two seconds, eight images were collected. The subject was positioned using a head brace.

The eight images were added together to produce the same image that would have occurred if multiple lights were turned on. Short movies were generated showing the subject under changing illumination. Forced choice questions were asked regarding each pair of movies. Among the questions were which subject exhibited fewer signs of aging and which was better looking. Movies compared were taken 30–60 minutes after normal application of the Sample A or Sample B formulations on two subjects. Nine observers compared products on subject 1 three times and on subject 2 five times.

Table I formula Sample A treated skin was found better looking in 51 of 71 comparisons. Further, Sample A treated skin showed fewer signs of aging with 49 votes of 71 total.

Statistical likelihood that the above results could have arisen from random guessing is less than 1% lousing the cumulative probability of getting 51/71 or 49/71 in 50% trials.

As each observer has a different reliability consistently answering a forced choice question, one can also weight the results by observer variability. Five of the 9 observers gave highly consistent results across trials, the other 4 performed more erratically. The reliable observers unanimously preferred the appearance of the Sample A cream in both questions.

Dermal Delivery Comparison

Skin delivery of a typical skin whitening agent (niacinamide) was measured after treatment according to three different dosing regimens comprised of the compositions in Tables I and II. These were the high stearic acid (Sample A) and low stearic acid (Sample B) formulas of the first and second compositions reported in the Tables. The three dosing regimens were 1.) Sample A-Sample A, 2.) Sample B-Sample A, and 3.) Sample B-Sample B, in which the second sample of each pair was applied twelve hours after the first sample of the pair. The samples were tested in vitro using by-product Yucatan piglet skin and Bronaugh flow-through cells. Dorsal skin from a female weanling Yucatan was shaved and sectioned to 380 $\mu$m thickness using a Padgett Dermatome® and mounted in Bronaugh diffusion cells with 0.64-cm$^2$ skin surface exposure (Crown Glass, Sommerville, N.J.). Skin barrier integrity was confirmed by trans-epidermal water loss measurement. The cells were maintained at 32° C. in cell warmers and the lower, dermal, skin surface was perfused with balanced salts buffer with bacteriostat at 8 ml/hour. Samples A and B were spiked with radiotracer 14C-niacinamide at 60 $\mu$Ci/gram and equilibrated for 72 hours. Homogenicity of radiotracer was confirmed by sampling aliquots from the top, middle and bottom of the vials.

The skin discs were dosed with 4 mg of the first product from each regimen pair, and spread on the 9-mm diameter exposed skin surface with a microcapillary glass rod. Seven replicates were dosed with the initial regimen component for each regimen pair, with the regimen pairs distributed equally among the sample warmers. After twelve hours of skin contact with the initial component of each regimen pair, the exposed skin surfaces were rinsed three times with approximately 1-ml of water and blotted dry with a cotton-tip applicator.

The skin discs were then dosed with the second product from each respective regimen pair in exactly the same way, ie. 4 mg of product spread on the exposed skin surface with a microcapillary glass rod. Following twelve hours of skin contact with the second component of each regimen pair, the skin surfaces were again rinsed three times with about 1-ml of water. The skin discs were then removed from the apparatus and blotted with Kim Wipe strips. The upper surfaces were tape-stripped ten times with Scotch® transparent tape to remove the non-viable stratum corneum barrier layer, and the epidermis was separated from the dermis with a scalpel. Epidermis was sonicated in 500 $\mu$L water, and dermis samples were digested with NCS tissue solubilizer. All samples were then analyzed for 14C-niacinamide in a solvent-appropriate scintillation cocktail using a Beckman 6500 liquid scintillation counter.

Results indicated that after the total 24-hour regimen, niacinamide deposition in the viable skin was greatest for the is Sample B-Sample A regimen, compared to Sample A-Sample A or Sample B-Sample B. The results suggest that alternate dosing with the low and high stearic base formulas exploits and synergizes the tissue deposition characteristics of the individual formulas to deliver maximum niacinamide skin lightening benefit compared to repetitive dosing with either the high stearic or low stearic base formulas alone. Results are presented In the Table below as percent of applied dose accumulated in each viable tissue compartment after the total 24 hours of regimen sample contact time.

|  | Accumulation Per Applied Dose Percent | | |
| --- | --- | --- | --- |
|  | Sample A-Sample A | Sample B-Sample A | Sample B-Sample B |
| Epidermis | 1.25 | 1.29 | 0.84 |
| Dermis | 0.70 | 1.29 | 1.19 |
| Total Viable Skin | 1.95 | 2.58 | 2.02 |

The foregoing description and example illustrate selected embodiments of the present invention.

What is claimed is:

1. A cosmetic skin lightening product delivered from a dual chamber package comprising:
   (A) a first composition within a first chamber of the dual chamber package, the composition comprising:
      (i) from about 15 to about 25% of stearic acid by weight of the first composition;
      (ii) from about 0.01 to about 10% of a skin lightening agent by weight of the first composition;
   (B) a second composition within a second chamber of the dual-chamber package, the second composition comprising:
      (i) from about 0.5 to about 4% of stearic acid by weight of the second composition;
      (ii) from about 0.01 to about 10% of a skin lightening agent by weight of the second composition; and
   wherein the stearic acid is present in a higher amount in the first than in the second composition.

2. The product according to claim 1 wherein the skin lightening agent is niacinamide.

3. The product according to claim 1 wherein each of the first and second compositions comprises from about 1 to about 40% by weight of a liquid oil emollient, the liquid oil emollient being present in a higher amount in the second than in the first composition.

4. The product according to claim 1, wherein the dual chamber package is provided with instructions to a consumer for separately but sequentially applying the first and second compositions to a skin treatment area.

5. The product according to claim 4 wherein the instructions further provide that the first composition remain on the treatment area during daytime and the second composition remain on the treatment area during nighttime.

* * * * *